United States Patent
Krijnen et al.

(10) Patent No.: US 7,800,309 B2
(45) Date of Patent: Sep. 21, 2010

(54) LOW-PRESSURE MERCURY VAPOR DISCHARGE LAMP AND APPARATUS FOR TREATMENT

(75) Inventors: Simon Krijnen, Roosendaal (NL); Theodorus Herman Ketelaar, Winschoten (NL); Olaf Mastenbroek, Roosendaal (NL); Roland Blasig, Kleve (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 403 days.

(21) Appl. No.: 11/719,777

(22) PCT Filed: Nov. 21, 2005

(86) PCT No.: PCT/IB2005/053842

§ 371 (c)(1),
(2), (4) Date: May 21, 2007

(87) PCT Pub. No.: WO2006/056934

PCT Pub. Date: Jun. 1, 2006

(65) Prior Publication Data

US 2009/0146569 A1    Jun. 11, 2009

(30) Foreign Application Priority Data

Nov. 24, 2004  (EP) .................................. 04106027

(51) Int. Cl.
*H01J 61/30* (2006.01)
(52) U.S. Cl. .................. 313/636; 313/493; 313/573
(58) Field of Classification Search .................. None
See application file for complete search history.

(56) References Cited

U.S. PATENT DOCUMENTS

| | | | |
|---|---|---|---|
| 4,048,537 A | 9/1977 | Blaisdell et al. | |
| 5,612,263 A | 3/1997 | Filmer et al. | |
| 5,751,007 A | 5/1998 | Weaver | |
| 5,925,582 A | 7/1999 | Filmer et al. | |
| 6,391,809 B1 | 5/2002 | Young | |
| 6,614,039 B2 * | 9/2003 | Hollander | 250/504 R |
| 2002/0103069 A1 | 8/2002 | Young | |

FOREIGN PATENT DOCUMENTS

| | | |
|---|---|---|
| DE | 1930057 | 12/1965 |
| DE | 19514602 A1 | 10/1996 |
| DE | 19836825 B4 | 2/2000 |
| DE | 19942696 A1 | 3/2000 |
| DE | 10204149 C1 | 7/2003 |
| EP | 0606897 A2 | 7/1994 |

(Continued)

*Primary Examiner*—Ashok Patel

(57) ABSTRACT

A low-pressure mercury vapor discharge lamp has a lamp envelope enclosing, in a gastight manner, a discharge space provided with a filling of mercury and a rare gas. The lamp envelope includes electrodes for maintaining a discharge in the discharge space. The lamp envelope transmits UV-light and is made of a black glass component. The composition of the black glass component is free of PbO and comprises, expressed as a percentage by weight, the following constituents: 65-70% by weight of $SiO_2$, 1.4-2.2% by weight of $Li_2O$, 1.5-2.5% by weight of $Na_2O$, 11-13% by weight of $K_2O$, 1.8-2.6% by weight of MgO, 2.5-5% by weight of CaO, 2-3.5% by weight of SrO, 8-9.5% by weight of BaO, 0.2-0.4% by weight of CoO, and 1.7-3.25% by weight of NiO.

8 Claims, 4 Drawing Sheets

FOREIGN PATENT DOCUMENTS

| | | |
|---|---|---|
| EP | 0650936 A1 | 5/1995 |
| JP | 08283038 A | 10/1996 |
| JP | 09188542 A * | 7/1997 |
| JP | 2003073142 A | 3/2003 |
| JP | 2004035389 A | 2/2004 |
| WO | WO9621629 A1 | 7/1996 |
| WO | WO2004005208 A1 | 1/2004 |

* cited by examiner though the envelope of the lamp is black. The black-light blue lamp should preferably not emit harmful UV-B (wavelength range 280-
LOW-PRESSURE MERCURY VAPOR DISCHARGE LAMP AND APPARATUS FOR TREATMENT The invention relates to a mercury vapor discharge lamp comprising a lamp envelope, the lamp envelope enclosing, in a gastight manner, a discharge space provided with a filling of mercury and a rare gas, the lamp envelope comprising discharge means for maintaining a discharge in the discharge space, the lamp envelope allowing passage of V-light, the lamp envelope being made of a black glass component, the composition of the black glass component being free of PbO.

The invention also relates to an apparatus for treatment with radiation for personal care, comprising a housing in which a Lw source is present and a wall made from a UV-transmitting material covering the housing, wherein the UV-source is the low-pressure mercury vapor discharge lamp.

In mercury vapor discharge lamps, mercury constitutes the primary component for the (efficient) generation of ultraviolet (UV) light. A luminescent layer comprising a luminescent material (for example, a fluorescent powder) may be present on the inner wall of the lamp envelope, also known as the discharge vessel, to convert UV into other wavelengths, for example, into UV-B and UV-A for tanning purposes (sun panel lamps) or into visible radiation for general illumination purposes. Such discharge lamps are therefore also referred to as fluorescent lamps. Alternatively, the ultraviolet light generated may be used for manufacturing germicidal lamps (LV-C). The lamp envelope of a low-pressure mercury vapor discharge lamp is usually tubular and circular in section and comprises both elongate and compact embodiments. Generally, the tubular lamp envelope of a so-called compact fluorescent lamp comprises a collection of relatively short straight parts having a relatively small diameter, which straight parts are connected together by means of bridge parts or arc-shaped parts. Compact fluorescent lamps are usually provided with an (integrated) lamp cap.

The lamp envelopes of mercury vapor discharge lamps, e.g. fluorescent lamps, are generally made of an inexpensive, so-called soda-lime type of glass. Compact fluorescent lamps are usually made of a lead-free Ba—Sr-rich glass. Apart from straight or bent parts, the lamp envelope may also include (two) so-called glass stems or end portions where the lamp envelope is hermetically sealed, said end portions enabling the current-supply conductors to pass through.

So-called black-light blue lamps emit predominantly UV-A radiation (wavelength range 320-380 nm) and a slightly visible violet-blue light. Such lamps contain mercury vapor in which, during operation of the lamp, a discharge is generated which is accompanied by the emission of characteristic mercury spectral lines. The inner wall of the lamp envelope is provided with a fluorescent powder that absorbs short-wave UV-B and lw-C radiation and, subsequently, emits said radiation predominantly in the form of long-wave UV-A radiation.

A so-called "black-light blue lamp" is used to cause certain materials to fluoresce by means of UV-A radiation; this is also referred to as photoluminescence. Photoluminescence is most clearly visible when the environment is dark. This is the reason why the lamp should preferably emit as little visible light as possible. This is achieved by making the glass of the lamp envelope absorb the greater portion of the emitted visible light. If the lamp is in the off-state, the glass of the lamp envelope is black. The glass does allow UV-A radiation and of some violet and blue light to pass, so that the burning lamp is of a dark violet-blue color. The black-light blue lamp should preferably not emit harmful UV-B (wavelength range 280-320 nm) and UV-C (wavelength range 100-280 nm) radiation; this radiation is almost completely absorbed by the fluorescent powder on the inner wall of the lamp envelope.

Black-light blue lamps are used, inter alia, for examining minerals, gems, stamps etc, and to detect falsifications such as counterfeit money, cheques, documents, and paintings. The lamps are also used to diagnose and treat skin diseases and to illuminate dance floors, for example in the form of disco lamps.

Previously, the glass of the existing black-light blue lamps comprised lead with a content of approximately 20% PbO by weight. A lamp made of this glass will be referred to as the "lead-containing black-light blue lamp" below. PbO has favorable properties in that it improves the processability and increases the electrical resistance of the glass. In addition, good maintenance results were observed with these lead-containing black-light blue lamps. However, a disadvantage of the use of PbO in black-light blue lamps is its toxicity. In the preparation of the lead glass, PbO is released into the atmosphere by atomization and evaporation, which has a harmful effect on the environment. PbO is also released when lead glass is subjected to a heat treatment, such as during "bridge-making", shaping, and fusing. Consequently, the working environment has to be adapted drastically to avoid exposure to PbO. Another disadvantage of PbO is the high price of the raw material. Yet another disadvantage of PbO is the reduction of the light output in compact fluorescent lamps, which is caused by evaporation and, subsequently, condensation of PbO on the fluorescent powder when the lead-containing tube glass is subjected to a hot working operation. This is the reason why a type of glass for a lamp envelope free of lead and yet having the desired physical melting, softening, expansion, and transmission properties has been investigated for a considerable length of time.

International application WO 96/21629 describes a lead-free black glass for use in an envelope of a black-light blue lamp which includes CoO in an amount of 0.45 to 1.0% by weight and NiO in an amount of 2.8 to 3.4% by weight. In the following, this glass will also be referred to as the "Filmer black" glass. The "Filmer" glass does not comprise PbO, $B_2O_3$, BaO, and $Sb_2O_3$. According to WO 96/21629, the glass can be exchanged with the existing lead-containing glasses for such envelopes. A burning lamp having such an envelope emits light of the same intensity and color as the existing lamp and emits predominantly UV-A radiation.

A drawback of the known low-pressure mercury vapor discharge lamp is the relatively poor maintenance of the lamp compared with the previously used PbO-containing black glasses.

The invention has for its object to eliminate the above disadvantage wholly or partly. According to the invention, this object is achieved by a mercury vapor discharge lamp comprising:

a lamp envelope enclosing, in a gastight manner, a discharge space provided with a filling of mercury and a rare gas, the lamp envelope comprising discharge means for maintaining a discharge in the discharge space, the lamp envelope allowing UV-light to pass, the lamp envelop being made of a black glass component, the composition of the black glass component being free of PbO and comprising, expressed as a percentage by weight, the following constituents:

| | |
|---|---|
| SiO$_2$ | 55-70 |
| MgO | 0.01-3 |
| CaO | 0.01-6 |
| CoO | 0.1-1 |
| NiO | 0.1-5 |
| Fe$_2$O$_3$ | 0.01-1 | the glass further comprising Li$_2$O, Na$_2$O, and K$_2$O, the sum of the concentrations of Li$_2$O, Na$_2$O, and K$_2$O being in the range from 13 to 18% by weight, the glass further comprising SrO and BaO, the sum of the concentrations of SrO and BaO being in the range from 8 to 13% by weight, further constituents of the glass being in the range from 0.01 to 0.3% by weight.

The glass according to the invention is free of PbO and is also free of other volatile, toxic, or corrosive components such as Sb$_2$O$_3$, As$_2$O$_3$, and F. In addition, the glass in accordance with the invention is free of B$_2$O$_3$ and ZrO$_2$. B$_2$O$_3$ is disadvantageous because it is expensive and aggressive relative to the refractory material of the glass furnace. ZrO$_2$ adversely affects the melting behavior of the glass.

As compared with the known "Filmer" glass, the glass according to the invention is a so-called sodium-poor glass. The known "Filmer" glass has a Na$_2$O content in the range of 14 to 18% by weight, whereas the glass according to the invention has a preferred Na$_2$O content in the range of 0.5 to 3% by weight. The use of a Na-poor glass composition according to the invention significantly reduces the mercury consumption of the lamp during life. The maintenance of the low-pressure mercury vapor discharge lamp is improved by the use of a sodium-poor glass.

The SiO$_2$ content of the glass in accordance with the invention is limited to 55 to 70% by weight. In combination with the other constituents, said SiO$_2$ content leads to a readily fusible glass. As is known in the art, SiO$_2$ serves as a network former. If the SiO$_2$ content is below 55% by weight, the cohesion of the glass and the chemical resistance are reduced. A SiO$_2$ content above 70% by weight hampers the vitrification process, causes the viscosity to become too high, and increases the risk of surface crystallization.

The substantial absence of Al$_2$O$_3$ has the following advantages. The liquidus temperature (T$_{liq}$) of the glass is reduced by at least 100° C. due to favorable crystallization properties. Al$_2$O$_3$ being practically absent in the glass composition according to the invention, as compared with that of the known "Filmer" glass composition, does not have a detrimental influence on the chemical resistance nor on the resistance to weathering of the glass. In addition, the glass according to the invention exhibits a low crystallization tendency as well as a viscosity and softening temperature (T$_{soft}$) that render a good processing of the glass possible.

The alkali metal oxides Li$_2$O, Na$_2$O, and K$_2$O are used as melting agents in the glass according to the invention, causing a reduction of the tile viscosity of the glass. If both alkali metal oxides are used in the above composition, then the so-called mixed-alkali effect causes the electrical resistance to be increased and T$_{liq}$ to be reduced. In addition, the alkali metal oxides predominantly determine the expansion coefficient α of the glass. This is favorable because it must be possible to seal the glass to the stem glass and/or the current supply conductors made, for example, of copper-plated iron/nickel wire in such a way that the glass is free from stress. If the alkali-metal-oxide content is below the indicated limits, the glass will have a too low α-value (coefficient of linear expansion), and T$_{soft}$ (softening point) will be too high. Above the indicated limits, the α-value becomes too high. Li$_2$O causes a greater reduction of T$_{soft}$ than K$_2$O, which is desirable for obtaining a wide so-called "Working Range" (=T$_{work}$-T$_{soft}$) of the glass. However, a too high Li$_2$O content leads to an excessive increase of T$_{liq}$. In addition, Li$_2$O is an expensive component, so that the Li$_2$O content is preferably limited, also for economic reasons.

BaO has the favorable property that it causes the electrical resistance of the glass to increase and T$_{soft}$ to decrease. Below 7% by weight BaO, the melting temperature (T$_{melt}$), the softening temperature (T$_{soft}$), and the working temperature (T$_{work}$) tend to increase too much. Above 10% by weight BaO, the liquidus temperature (T$_{liq}$) and accordingly the crystallization tendency of the glass increase too much.

The alkaline earth metal oxides SrO, MgO, and CaO have the favorable property that they lead to a reduction of T$_{melt}$.

The chemical components that give color to the glass, also denoted chromophores, are NiO, CoO, and Fe$_2$O$_3$. These chromophores are added to the glass composition according to the invention in concentrations such that the color of the glass envelope and the UV-A output of the resulting glass are at least comparable to those of the lead-containing glass of the prior art black-light blue lamps.

CoO absorbs green to red light (500-700 nm) and NiO absorbs blue to green light (400-550 nm). Both components have the advantage that they absorb little UV-A radiation around 365 nm. However, both components are very expensive and hence are added in the lowest possible concentrations. The Co and Ni concentrations are selected such that a VIS/UV-A output is obtained analogous to that of the "Filmer" black-light blue lamp and of the lead-containing black-light blue lamp.

A NiO content above the indicated limit leads to too low a transmission at a wavelength of 404.7 nm (one of the Hg spectral lines), so that a burning lamp having an envelope of this glass will be of a color which differs from that of an existing lamp. In addition, the UV-A absorption increases too much above the indicated limit.

A CoO content above the indicated limit leads to a different color of the lamp, i.e. the lamp becomes darker and more bluish in color. In addition, the infrared transmission of the glass will decrease, as a result of which shaping of the glass becomes more difficult. A higher concentration of CoO also leads to a higher UV-A absorption.

The addition of Fe$_2$O$_3$ to the glass according to the invention has a favorable influence on the absorption of harmful UV-B radiation.

A preferred embodiment of the low-pressure mercury vapor discharge lamp according to the invention is characterized in that the composition of the glass component comprises, expressed as a percentage by weight:

| | |
|---|---|
| SiO$_2$ | 65-70 |
| Li$_2$O | 1.4-2.2 |
| Na$_2$O | 1.5-2.5 |
| K$_2$O | 11-13 |
| MgO | 1.8-2.6 |
| CaO | 2.5-5 |
| SrO | 2-3.5 |
| BaO | 8-9.5 |
| CoO | 0.2-0.4 |
| NiO | 1.7-3.25 |
| Fe$_2$O$_3$ | 0.1-0.2. |

The glass in accordance with the preferred embodiment of the invention has a Na$_2$O content in the range of 1.5 to 2.5% by weight, whereas the preferred embodiment of the known "Filmer" glass has a Na$_2$O content in the range of 16.7 to 17.3% by weight. The mercury consumption of the lamp during life is significantly reduced and the maintenance of the low-pressure mercury vapor discharge lamp is improved by the use of a sodium-poor glass composition.

The concentrations of the chromophores CoO and NiO in the preferred glass composition are lower than in the known "Filmer" glass. These concentrations are chosen such that the color of the glass envelope and the UV-A output of the resulting glass match the requirements for black-light blue lamps.

The preferred glass composition has a favorable $T_{liq} \leq 800°$ C. and hardly tends towards crystallization during the manufacture of the glass and during drawing of glass tubing from said glass. By keeping the concentrations in the preferred ranges and by virtue of a wide Working Range of at least 310° C. and a low $T_{soft}$ (700° C.), the glass can be shaped into a tube without any problems by means of, for example, the Danner or the Vello process, which are known in the art.

The glass in accordance with the preferred embodiment of the invention has favorable fusion and processing properties. The linear expansion coefficient ($\alpha$) can be tuned to match the glass with other glasses. In addition, the other physical parameters can be chosen approximately equal to those of the known "Filmer" glass. The glass composition according to the preferred embodiment of the invention is very suitable for drawing glass tubing and for use as a lamp envelope or stem in a fluorescent lamp.

The glass in accordance with the invention can be refined by means of Na$_2$SO$_4$. To this end, a preferred embodiment of the low-pressure mercury vapor discharge lamp according to the invention is characterized in that the composition of the glass component in addition comprises 0.01 to 0.2% by weight of SO$_3$. The known "Filmer" glass uses antimony fining (Sb$_2$O$_3$). The use of sulphate/carbon refining during production of the glass according to the invention renders possible a reduction in the concentrations of the chromophores CoO and NiO in the glass. Sulphate/carbon refining serves to avoid the use of toxic antimony compounds and other toxic refining agents.

The glass composition may additionally contain up to 0.5% by weight of CeO$_2$, preferably less than 0.2% by weight of CeO$_2$, for absorbing undesirable UV radiation.

Preferably, the sum of the concentrations of Li$_2$O, Na$_2$O, and K$_2$O is in the range from 14 to 16% by weight. Preferably, the sum of the concentrations of SrO and BaO is in the range from 10 to 12.5% by weight. The coefficient of linear expansion a of the preferred glass composition has favorable properties if the concentrations are kept within the preferred ranges.

The glass composition in accordance with the invention can be refined by means of Na$_2$SO$_4$, so that the glass may contain up to 0.2% by weight of SO$_3$. The glass may additionally contain an impurity in the form of approximately 0.5% by weight of Fe$_2$O$_3$, preferably less than 0.2% by weight of Fe$_2$O$_3$, which originates from the raw materials used. If necessary, up to 0.5% by weight of CeO$_2$, preferably less than 0.2% by weight of CeO$_2$, is added to the glass to absorb undesirable UV radiation.

A protective coating such as, for example, an Al$_2$O$_3$ coating, can be dispensed with because of the low sodium-content of the glass composition according to the invention. Such protective coatings lead to a loss in light transmission, which is undesirable.

Low-pressure mercury vapor discharge lamps with UV-A and UV-B luminescent materials are employed in an apparatus for treatment with radiation for personal care, in particular for tanning purposes. A typical tanning unit comprises an array of tanning lamps emitting UV-radiation in the direction of the (human) body positioned in the vicinity of the low-pressure mercury vapor discharge lamps. During a tanning session, people need to wear special glasses for protecting their eyes against the UV radiation. There is no entertainment, except for a radio in some cases, during the session, which have a typical duration of approximately 10 to 30 minutes. It is desirable that during a tanning session the user should be able to read a book, watch television, or play games. Because of the high level of visual radiation of tanning lamps, it is not possible to watch a screen, since the contrast would be very low. To obviate this, the invention also relates to an apparatus for treatment with radiation for personal care, comprising a housing in which a UV source is present and a wall made from a UV-transmitting material covering the housing, wherein the UV-source is the low-pressure mercury vapor discharge lamp according to the invention, the glass comprising the constituents as described in the description and claims of the present patent application.

The use of the black-light blue lamp according to the invention in the apparatus for treatment with radiation for personal care substantially removes the visual radiation by filtering the radiation produced inside the tanning lamp. As a result, the visual light level is strongly reduced, and the contrast of a display device is enhanced. The luminescent materials in the low-pressure mercury vapor discharge lamp are chosen such that the required amounts of UV-A and UV-B radiation are radiated towards the (human) body. For protection, the user wears transparent glasses, for example made from polycarbonate, which reduce the UV radiation incident on the eye without impairing the effect of visible radiation.

These and other aspects of the invention are apparent from and will be elucidated with reference to the embodiments described hereinafter.

In the drawings.

The Figures are purely diagrammatic and not drawn to scale. Some dimensions are particularly strongly exaggerated for the sake of clarity. Similar components in the Figures are denoted as much as possible by the same reference numerals.

Figure 1:
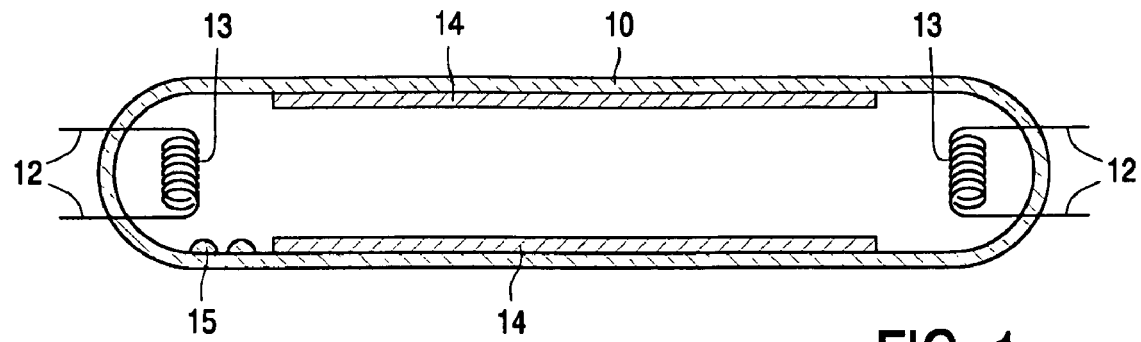
FIG. 1 is a cross-sectional view of a low-pressure mercury-vapor discharge lamp with a lamp envelope made from a glass with a composition in accordance with the invention.

FIG. 1 is a highly diagrammatic sectional view of a low-pressure mercury-vapor discharge lamp with a tubular lamp envelope 10 which is circular in cross-section and which is made of a glass having a composition in accordance with the invention. Current-supply conductors 12 which are connected to electrodes 13 issue from the lamp envelope 10. Each of the electrodes 13 in FIG. 1 comprises a winding of tungsten coated with an electron-emissive material, here a mixture of barium oxide, calcium oxide, and strontium oxide. A layer of a fluorescent material (phosphors) 14 is provided on the inner surface of the lamp envelope 10. Metallic mercury 15, which evaporates after ignition of the lamp, is present within the lamp envelope 10. Before such a lamp is sealed off, it is filled with argon having a pressure of approximately 700 Pa. In an alternative embodiment of the low-pressure mercury vapor discharge lamp, the lamp envelope is provided with an amalgam.

Figure 2:
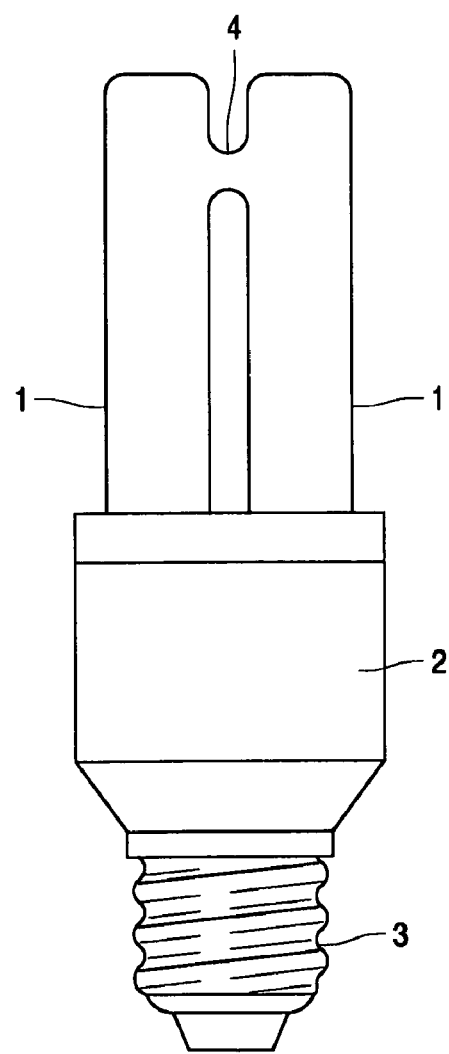
FIG. 2 is a side elevation of a compact fluorescent lamp with a lamp envelope made from a glass with a composition in accordance with the invention.

FIG. 2 is a schematic side view of a compact fluorescent lamp. The lamp is composed of four thin parallel lamp envelopes 1 (only two of which are shown in the drawing) which are made of a glass having a composition in accordance with the invention. The lamp envelopes 1 are interconnected by a bridge 4. The lamp also comprises a lamp base 2 for accommodating electronic circuitry and a threaded lamp holding means 3 which is to be installed in a luminaire and through which the mains voltage is supplied. The substantial wall load makes the use of a glass according to the invention particularly advantageous.

A glass of a composition according to a particularly favorable embodiment (see Table I) was prepared, comprising 63.6% by weight of $SiO_2$, 0.04% by weight of $Al_2O_3$, 1.9% by weight of $Li_2O$, 2.7% by weight of $Na_2O$, 11.3% by weight of $K_2O$, 2.9% by weight of MgO, 4.1% by weight of CaO, 2.1% by weight of SrO, 8.6% by weight of BaO, 0.43% by weight of CoO, 1.96% by weight of NiO, and 0.14% by weight of $Fe_2O_3$. Owing to the sulphate/carbon refining process, the favorable glass composition comprises 0.2% by weight of $SO_3$.

The sum of the concentrations of $Li_2O$, $Na_2O$, and $K_2O$ in this embodiment of the glass composition is approximately 15.9% by weight, and the sum of the concentrations of SrO and BaO is approximately 10.7% by weight, giving the glass a relatively low cost price. The melting operation is carried out in an electrical gas-fired furnace at 1450° C. The starting materials used are quartz sand, dolomite ($CaCO_3 \cdot MgCO_3$), the carbonates of Li, Na, K, Sr, and Ba, and CoO/NiO and $Fe_2O_3$. The refining agent used is $Na_2SO_4$ and carbon. No particular problems occur during melting and further processing. For comparison, Table I shows an example of a glass having a low sodium content in accordance with the known "Filmer" glass as described in International application WO 96/21629.

TABLE I

Glass composition according to a particularly favorable embodiment of the invention

| | composition in % by weight | |
|---|---|---|
| constituents | glass in accordance with the invention | glass in accordance with WO 96/21629 |
| $SiO_2$ | 63.6 | 68.3 |
| $Al_2O$ | 0.04 | 1.7 |
| $Li_2O$ | 1.9 | — |
| $Na_2O$ | 2.7 | 17.0 |
| $K_2O$ | 11.3 | 1.1 |
| MgO | 2.9 | 3.3 |
| CaO | 4.1 | 4.7 |
| SrO | 2.1 | — |
| BaO | 8.6 | — |
| CoO | 0.43 | 0.55 |
| NiO | 1.96 | 2.9 |
| $Fe_2O_3$ | 0.14 | 0.07 |
| $SO_3$ | 0.2 | 0.2 |

Table II gives the physical properties of the glass composition according to the invention as compared with the known glass composition.

TABLE II

Physical properties of the glass compositions of Table I.

| | composition in % by weight | |
|---|---|---|
| properties | glass in accordance with the invention | glass in accordance with WO 96/21629 |
| $10^6 \times \alpha_{25\text{-}300}$ | 9.4 | 10.3 |
| $T_{strain}$ (° C.) | 492 | 480 |
| $T_{ann}$ (° C.) | 520 | 520 |
| $T_{soft}$ (° C.) | 691 | 680 |
| $T_{work}$ (° C.) | 982 | 975 |
| $T_{melt}$ (° C.) | 1,283 | 1,400 |
| $T_{K100}$ (° C.) | 377 | 175 |
| $T_{rho}$ (° C.) | 476 | 510 |
| s.m. (kg/m³) | 2,682 | 2,530 |

The symbols in Table II have the following meanings:

$\alpha_{25\text{-}300}$ ... ($10^{-6}$/° C.): average coefficient of linear expansion between 25° C. and 300° C.;

$T_{strain}$ (° C.): temperature at which η (viscosity)=$10^{14.5}$ dPa.s, termed strain point;

$T_{ann}$ (° C.): temperature at which η=$10^{13.0}$ dPa.s, termed annealing point;

$T_{soft}$ (° C.): temperature at which η=$10^{7.6}$ dPa.s, termed softening point;

$T_{work}$ (° C.) temperature at which η=$10^{4.0}$ dPa.s, termed working temperature;

$T_{melt}$ (° C.): temperature at which η=$10^{2.0}$ dPa.s, termed melting point;

rho (ohm.cm): specific resistance;

$T_{K100}$ (° C.) temperature at which rho=$10^8$ ohm.cm;

$T_{rho}$ (° C.): temperature at which rho=$10^{6.52}$ ohm.cm;

s.m. (kg/dm³): specific mass.

The striking result of the comparison of glass compositions in Table II is that all physical properties are approximately the same for the glass composition in accordance with the invention and for the known glass composition. The deviating value for $T_{K100}$ will be explained below.

The glass according to the invention being sodium poor, the mercury consumption of mercury vapor discharge lamps made from the glass with a composition according to the invention is substantially less than that of mercury vapor discharge lamps made from the known "Filmer" glass. The use of the glass according to the invention leads to a significantly reduced mercury consumption in the lamp. The use of the glass according to the invention makes an internal protective coating of, for example, $Al_2O_3$ or $Y_2O_3$ unnecessary.

Figure 3:
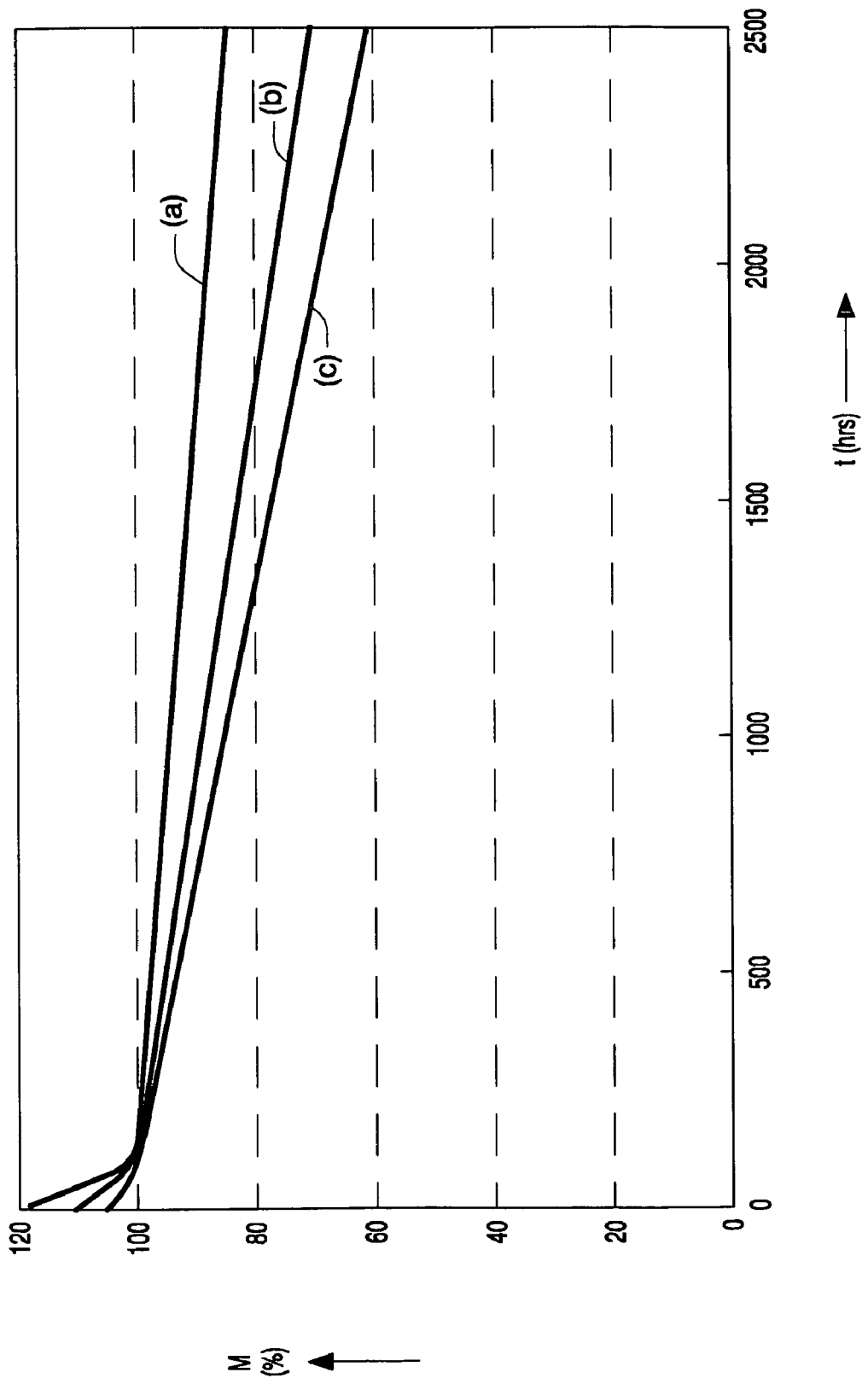
FIG. 3 shows the maintenance (% UV-A radiation) as a function of time of a low-pressure mercury-vapor discharge lamp with a lamp envelope made from a glass with a composition in accordance with the invention as compared with a lamp envelope made from the known "Filmer" glass.

FIG. 3 is shows the maintenance M (in % UV-A radiation) as a function of time of a low-pressure mercury-vapor discharge lamp with a lamp envelope made from a glass with a composition in accordance with the invention (curve a) compared with a lamp envelope made of the "lead-containing black-light blue lamp" (curve b) and compared with a lamp envelope made from the known "Filmer" glass (curve c). The reference point is the maintenance at 100 hours. It can be seen that after 2000 hours the maintenance of the "Filmer" glass (curve c) has dropped to approx. 62%, the maintenance of the glass of the "lead-containing black-light blue lamp" (curve b) has dropped to approx. 74%, whereas the maintenance of the glass according to the invention has only dropped to 88%.

Figure 4:
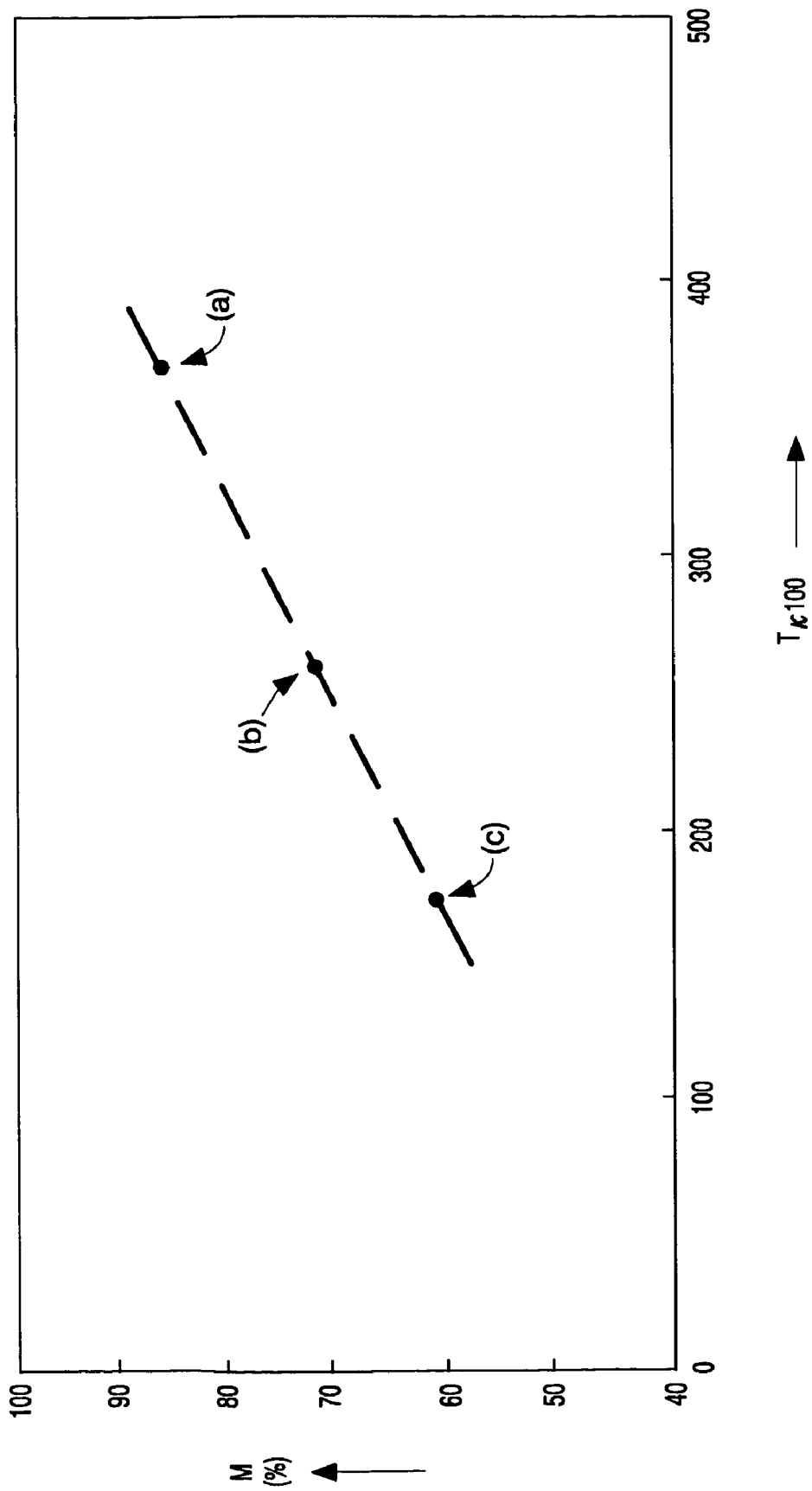
FIG. 4 shows the maintenance of a low-pressure mercury vapor discharge lamp with a lamp envelope made from a glass with a composition in accordance with the invention as a function of the glass resistivity.

FIG. 4 shows the maintenance of a low-pressure mercury vapor discharge lamp with a lamp envelope made from a glass with a composition in accordance with the invention as a function of the glass resistivity. The ion mobility in a glass is correlated with its electrical resistivity: a low electrical resistivity resulting in a high ion mobility. The higher the ion mobility, the more sodium ions can diffuse to the inner glass surface to react with mercury, a well-known cause of mercury consumption during lamp life time. Mercury consumption leads to a lower lamp maintenance, being the UV output of the lamp relative to its initial output (measured at 100 hours). Overall, it can be stated that the higher the ion mobility, the lower the lamp maintenance. The glass resistivity, correlated to the ion mobility, is expressed as the $T_{K100}$, which is the temperature at which the glass has a resistivity of $10^6$ Ohm.m. It is noted that the conductivity of glass is temperature-dependent. In general, the higher glass resistivity, the higher the $T_{K100}$ will be, or the higher the $T_{K100}$, the higher the lamp maintenance will be. The point referenced "a" refers to the glass composition according to the invention (cf. curve a in FIG. 3). The point referenced "b" refers to the glass composition of the "lead-containing black-light blue lamp" (cf. curve b in FIG. 3). The point referenced "c" refers to the glass composition of the "Filmer" glass (cf. curve c in FIG. 3).

Figure 5:
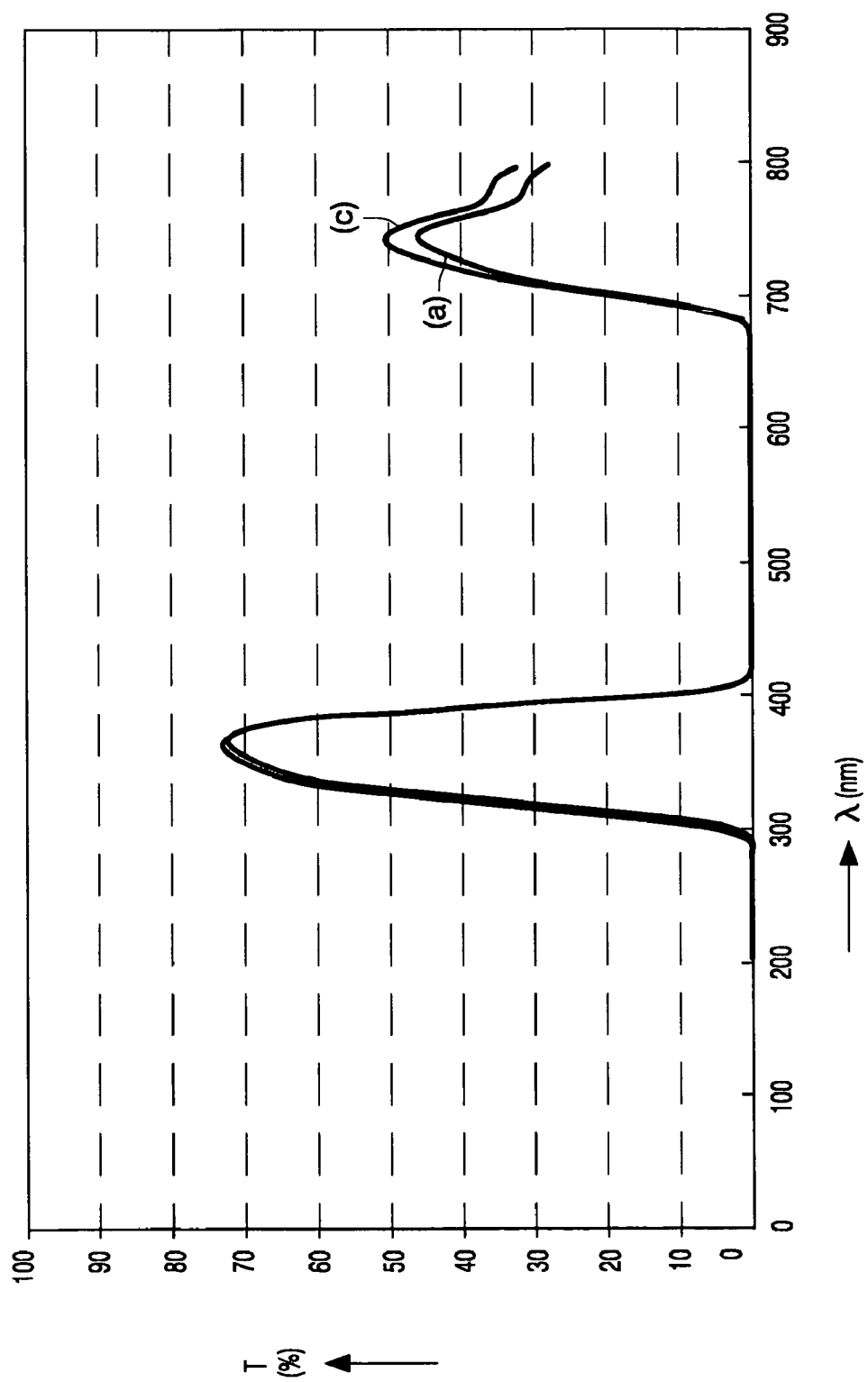
FIG. 5 shows the transmission of the glass of according to the invention as compared to that of the known "Filmer" glass.

FIG. 5 shows the transmission (curve a) of the glass of the invention compared with the transmission (curve c) of the known "Filmer" glass. It can be seen that the transmission curves practically overlap. Compared with the known "Filmer" glass, the glass according to the invention is a so-called sodium-poor glass. The known "Filmer" glass has a $Na_2O$ content in the range of 14 to 18% by weight, whereas the glass according to the invention has a preferred $Na_2O$ content in the range of 0.5 to 3% by weight. The use of a Na-poor glass composition according to the invention significantly reduces the mercury consumption of the lamp during life. The maintenance of the low-pressure mercury vapor discharge lamp is improved by the use of a sodium-poor glass.

Preferably, the black-light blue lamp according to the invention is used in an apparatus for treatment with radiation for personal care. Filtering of the radiation produced inside the tanning lamp substantially removes the visual radiation emitted by the low-pressure mercury vapor discharge lamps in the apparatus for treatment with radiation for personal care. It thus becomes possible to read a book or to watch an informative program, a film, or any other form of entertainment on a display device, e.g. a standard television set, a liquid crystal display device, or a plasma display device arranged in the interior of the apparatus for treatment with radiation for personal care.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A mercury vapor discharge lamp comprising:
a lamp envelope enclosing, in a gastight manner, a discharge space provided with a filling of mercury and a rare gas,
the lamp envelope comprising discharge means for maintaining a discharge in the discharge space,
the lamp envelope allowing UV-light to pass,
the lamp envelope being made of a black glass component, the composition of the black glass component being free of PbO and comprising, expressed as a percentage by weight, the following constituents:

| | |
|---|---|
| $SiO_2$ | 55-70 |
| MgO | 0.01-3 |
| CaO | 5.1-6 |
| CoO | 0.2-0.4 |
| NiO | 1.7-3.25 |
| $Fe_2O_3$ | 0.01-1 | the black glass component further comprising $Li_2O$, $Na_2O$, and $K_2O$, the sum of the concentrations of $Li_2O$, $Na_2O$, and $K_2O$ being in the range from 13 to 18% by weight,
the black glass component further comprising SrO and BaO, the sum of the concentrations of SrO and BaO being in the range from 8 to 13% by weight.

2. The mercury vapor discharge lamp as claimed in claim 1, wherein the composition of the black glass component comprises:

$Fe_2O_3$ 0.1-0.2.

3. The mercury vapor discharge lamp as claimed in claim 1, wherein the composition of the black glass component comprises:

| | |
|---|---|
| $SiO_2$ | 65-70 |
| $Li_2O$ | 1.4-2.2 |
| $Na_2O$ | 1.5-2.5 |
| $K_2O$ | 11-13 |
| MgO | 1.8-2.6 |
| SrO | 2-3.5 |
| BaO | 8-9.5. |

4. The mercury vapor discharge lamp as claimed in claim 1, wherein the composition of the black glass component in addition comprises: 0.01 to 0.2% by weight of $SO_3$.

5. An apparatus for treatment with radiation for personal care, comprising a housing in which a UV source is present and a wall made from an UV transmitting material covering the housing, wherein the UV source is the low-pressure mercury vapor discharge lamp as claimed in claim 1.

6. The mercury vapor discharge lamp of claim 1, wherein the black glass component further comprises $CeO_2$ from more than 0.2% to less than 0.5% by weight.

7. A mercury vapor discharge lamp comprising:
a lamp envelope enclosing a discharge space provided with a filling of mercury and a rare gas; and
electrodes for maintaining a discharge in the discharge space;
wherein the lamp envelope is configured to allow UV-light to pass, and comprises a black glass component free of PbO and comprising, expressed as a percentage by weight, the following constituents:

| | |
|---|---|
| SiO$_2$ | 63.6 |
| Li$_2$O | 1.9 |
| Na$_2$O | 2.7 |
| K$_2$O | 11.3 |
| MgO | 2.9 |
| CaO | 5.1-6 |
| SrO | 2.1 |
| BaO | 8.6 |
| CoO | 0.43 |
| NiO | 1.96 |
| Fe$_2$O$_3$ | 0.14 |
| SO$_3$ | 0.2. |

8. The mercury vapor discharge lamp of claim 7, wherein the black glass component further comprises CeO$_2$ from more than 0.2% to less than 0.5% by weight.

* * * * *